(12) United States Patent
Farzin-Nia et al.

(10) Patent No.: US 8,568,138 B2
(45) Date of Patent: Oct. 29, 2013

(54) AESTHETIC SELF-LIGATING ORTHODONTIC BRACKET

(75) Inventors: Farrokh Farzin-Nia, Inglewood, CA (US); Albert Ruiz-Vela, Alta Loma, CA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 13/371,869

(22) Filed: Feb. 13, 2012

(65) Prior Publication Data

US 2012/0141948 A1    Jun. 7, 2012

Related U.S. Application Data

(63) Continuation of application No. 11/947,168, filed on Nov. 29, 2007, now Pat. No. 8,113,827, which is a continuation of application No. 10/643,181, filed on Aug. 18, 2003, now Pat. No. 7,419,375.

(60) Provisional application No. 60/404,345, filed on Aug. 19, 2002.

(51) Int. Cl.
   *A61C 3/00*    (2006.01)

(52) U.S. Cl.
   USPC .......................................... 433/10

(58) Field of Classification Search
   USPC ..................................... 433/8–24
   See application file for complete search history.

(56) References Cited

U.S. PATENT DOCUMENTS

| | | | | |
|---|---|---|---|---|
| 2,549,528 A * | 4/1951 | Russell | ........................... | 433/13 |
| 4,652,165 A * | 3/1987 | Bertesi et al. | ..................... | 402/4 |
| 5,322,435 A * | 6/1994 | Pletcher | ........................... | 433/11 |
| 5,466,151 A * | 11/1995 | Damon | .............................. | 433/10 |
| 5,474,446 A * | 12/1995 | Wildman et al. | ............... | 433/14 |
| 6,071,118 A * | 6/2000 | Damon | .............................. | 433/9 |
| 6,257,883 B1 * | 7/2001 | Voudouris | ....................... | 433/11 |
| 2002/0110778 A1 * | 8/2002 | Abels et al. | .................... | 433/11 |
| 2002/0132206 A1 * | 9/2002 | Voudouris | ....................... | 433/11 |
| 2003/0049582 A1 * | 3/2003 | Abels et al. | .................... | 433/11 |
| 2004/0072119 A1 * | 4/2004 | Voudouris | ....................... | 433/11 |
| 2005/0239012 A1 * | 10/2005 | Bathen et al. | ................... | 433/10 |

FOREIGN PATENT DOCUMENTS

| | | |
|---|---|---|
| DE | 4434209 A1 | 3/1996 |
| EP | 0 623 320 A1 | 11/1994 |
| WO | 2004006797 A2 | 1/2004 |

OTHER PUBLICATIONS

European Patent Office, Notice of Opposition issued in related European application No. 042501411 dated Aug. 7, 2012.

* cited by examiner

*Primary Examiner* — Todd Manahan
*Assistant Examiner* — Matthew Nelson
(74) *Attorney, Agent, or Firm* — Wood, Herron & Evans, LLP

(57) ABSTRACT

A self-ligating orthodontic bracket for captivating an archwire with a tooth. The bracket includes a bracket body mountable to a tooth and a self-ligating mechanism having an archwire slot and a ligating slide. The ligating slide is movable between an open position in which an archwire is insertable into the archwire slot and a closed position in which the archwire is retained in the archwire slot. The bracket body may be formed from a non-metallic material, such as a polymer, a filled polymer composite, or a ceramic, and the self-ligating mechanism may be formed from a metal. The bracket may include a resilient engagement member with a detent positioned to engage an aperture or throughhole extending through the ligating slide when the ligating slide is in the closed position.

14 Claims, 8 Drawing Sheets

US 8,568,138 B2

AESTHETIC SELF-LIGATING ORTHODONTIC BRACKET

CROSS-REFERENCE TO RELATED APPLICATIONS

This application is a continuation of Ser. No. 11/947,168, filed Nov. 29, 2007, which is a continuation of application Ser. No. 10/643,181, filed on Aug. 18, 2003, which claims the benefit of U.S. Provisional Application No. 60/404,345, filed on Aug. 19, 2002, the disclosure of each of which is hereby incorporated by reference herein in its entirety.

FIELD OF THE INVENTION

The invention relates generally to orthodontic brackets and, more particularly, to self-ligating orthodontic brackets.

BACKGROUND OF THE INVENTION

Orthodontic brackets represent a principal component of all corrective orthodontic treatments devoted to improving a patient's occlusion. Conventional orthodontic treatments affix brackets to the patient's teeth and an archwire is threaded through a slot of each bracket. The archwire applies corrective forces that coerce the teeth to move to orthodontically correct positions. Traditional ligatures, such as small elastomeric O-rings or fine metal wires, are employed to retain the archwire within each bracket slot. Due to difficulties encountered in applying an individual ligature to each bracket, self-ligating orthodontic brackets have been developed that eliminate the need for ligatures by relying on a movable latch or slide for captivating the archwire with the bracket slot.

Conventional orthodontic brackets are ordinarily formed from stainless steel, which is strong, nonabsorbent, weldable, and relatively easy to form and machine. Patients undergoing orthodontic treatment using metal orthodontic brackets, however, may be embarrassed by the visibility of conventional metal orthodontic brackets, which are not cosmetically pleasing. To improve the cosmetic appearance, certain conventional orthodontic brackets incorporate a bracket body of a transparent or translucent non-metallic material, such as a polymer resin or a ceramic, that assumes or mimics the color or shade of the underlying tooth. Such orthodontic brackets may rely upon a metallic insert lining the archwire slot for strengthening and reinforcing the bracket body in the vicinity of the archwire slot. As a result, the appearance of metal in the patient's mouth is less noticeable in ordinary view and, therefore, brackets characterized by a non-metallic bracket body are more aesthetically pleasing. However, conventional orthodontic brackets with non-metallic bracket bodies have yet to implement self-ligation as self-ligating brackets necessitate the use of metallic materials because of the strength, ductility and toughness of metals as compared to other non-metallic materials.

Conventional self-ligating orthodontic brackets suffer from other deficiencies. For example, certain self-ligating brackets apply a spring force to hold a ligating slide in a closed position to captivate an archwire. When the ligating slide is moved from the closed position to an open position, the spring force continues to act against the ligating slide and opposes the movement.

Thus, there would be a need for a self-ligating orthodontic bracket that overcomes these deficiencies of conventional self-ligating orthodontic brackets.

SUMMARY OF THE INVENTION

The invention overcomes the foregoing and other shortcomings and drawbacks of conventional self-ligating orthodontic brackets, as described above. According to the principles of the invention, an orthodontic bracket includes a bracket body configured to be mounted to a tooth and a metallic self-ligating assembly carried by the bracket body including an archwire slot and a ligating member movable between an open position in which an archwire is insertable into the archwire slot and a closed position in which the archwire is retained in the archwire slot. The bracket body is formed from a non-metallic material, such as a polymer, a filled polymer composite, or a ceramic. In accordance with the principles of the invention, the metallic insert includes a self-ligating member, which differs from conventional orthodontic brackets having non-metallic bracket bodies in which the metallic insert merely operates as a liner for the archwire slot.

In accordance with another embodiment of the invention, a self-ligating orthodontic bracket includes a bracket body configured to be mounted to a tooth and a ligating slide carried by the bracket body for movement between an open position in which an archwire is insertable into an archwire slot of the bracket body and a closed position in which the ligating slide retains the archwire in the archwire slot. The self-ligating orthodontic bracket further includes a resilient engagement member positioned to engage a recess or throughhole in the ligating slide when the ligating slide is in the closed position. The engagement between the resilient engagement member and recess effectively constrains movement of the ligating slide relative to the bracket body.

In accordance with yet another embodiment of the invention, a self-ligating orthodontic bracket includes a ligating slide and a bracket body configured to be mounted to a tooth. The bracket body has an archwire slot and a pair of opposed guides supporting the ligating slide. The guides operate to guide the ligating slide for movement between an open position in which an archwire is insertable into the archwire slot and a closed position in which the archwire is retained in the archwire slot. At least one of the guides includes a recess or throughhole capable of being engaged by a resilient engagement member when the ligating slide is in the closed position for constraining movement of the ligating slide relative to the bracket body.

In accordance with yet another embodiment of the invention, an apparatus for coupling an archwire with a tooth includes a bracket body configured to be mounted to a tooth and a ligating slide carried by the bracket body for movement between an open position in which an archwire is insertable into an archwire slot in the bracket body and a closed position in which the ligating slide retains the archwire in the archwire slot. The ligating slide includes a rear surface facing the tooth, a front surface opposite to the rear surface, and an aperture or throughhole extending from the front surface to the rear surface. A resilient engagement member is capable of engaging the ligating slide in the closed position for constraining movement of the ligating slide relative to the bracket body. The apparatus further includes a tool including a shoulder and a tip projecting from the shoulder by a distance sufficient to deflect the resilient engagement member so that the ligating slide may be moved from the closed position to the open position when the shoulder contacts a portion of the ligating slide surrounding the aperture.

In accordance with yet another embodiment of the invention, a self-ligating orthodontic bracket includes a bracket body configured to be mounted to a tooth and a ligating slide carried by the bracket body for movement between an open position in which an archwire is insertable into an archwire slot of the bracket body and a closed position in which the ligating slide retains the archwire in the archwire slot. The ligating slide includes a rear surface facing the tooth, a front surface opposite to the rear surface, and a tool-engaging element accessible from the front surface. The front surface of the ligating slide has a channel effective for guiding the movement of a tool contacting the front surface and moving toward the tool engaging element.

In accordance with yet another embodiment of the invention, a self-ligating orthodontic bracket includes a bracket body configured to be mounted to a tooth and a ligating slide carried by the bracket body for movement between an open position in which an archwire is insertable into an archwire slot in the bracket body and a closed position in which the ligating slide retains the archwire in the archwire slot. The orthodontic bracket further includes a deflecting element on the bracket body that deflects objects in a patient's oral cavity away from a peripheral edge of the ligating slide when the ligating slide is in the closed position and the bracket body is mounted to the tooth.

In accordance with yet another embodiment of the invention, a self-ligating orthodontic bracket includes a bracket body configured to be mounted to a tooth and a ligating slide carried by the bracket body for movement between an open position in which an archwire is insertable into an archwire slot in the bracket body and a closed position in which the ligating slide retains the archwire in the archwire slot. The ligating slide includes at least one stop element that abuts a stop element on the bracket body when the ligating slide is in the open position.

The above and other objects and advantages of the invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION

Although the invention will be described next in connection with certain embodiments, the invention is not limited to practice in any one specific type of self-ligating orthodontic bracket. The description of the embodiments of the invention is intended to cover all alternatives, modifications, and equivalent arrangements as may be included within the spirit and scope of the invention as defined by the appended claims. In particular, those skilled in the art will recognize that the components of the embodiments of the invention described herein could be arranged in multiple different ways.

Figure 1:
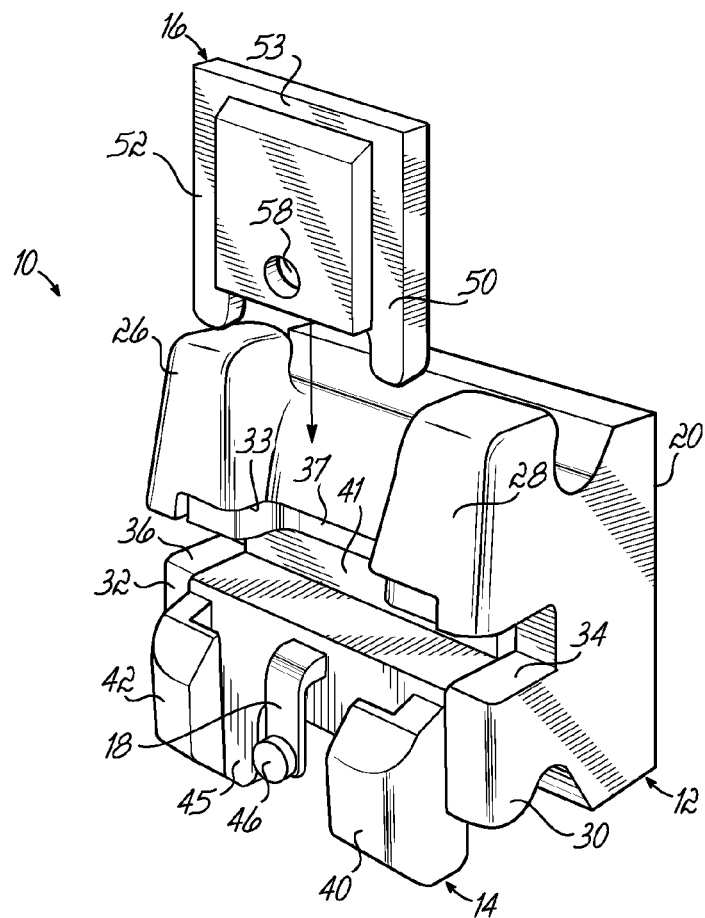
FIG. 1 is a perspective view of a self-ligating orthodontic bracket according to the principles of the invention in which the ligating slide is removed from the assembly for clarity.
Figure 2:
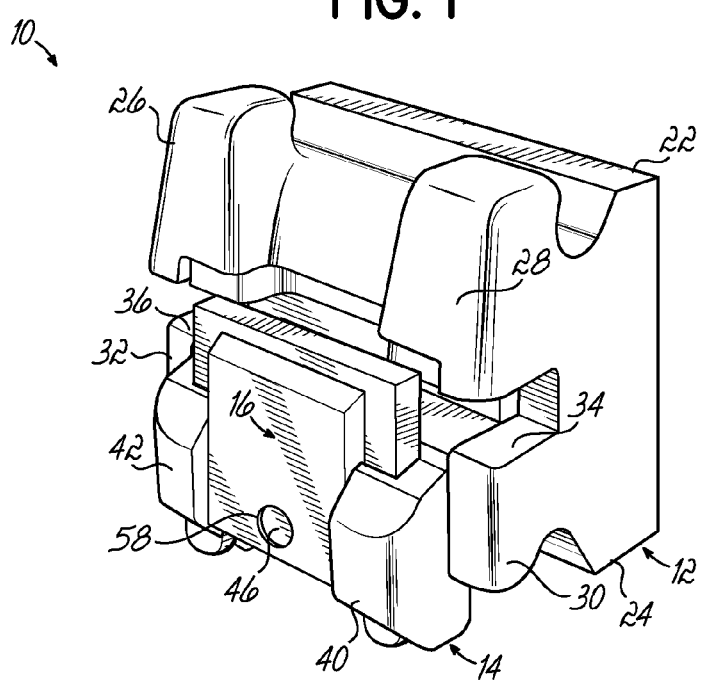
FIG. 2 is a perspective view of the self-ligating orthodontic bracket of FIG. 1 in which the movable slide is in a latched condition for capturing an archwire, not visible in FIG. 2, in the archwire slot.
Figure 3:
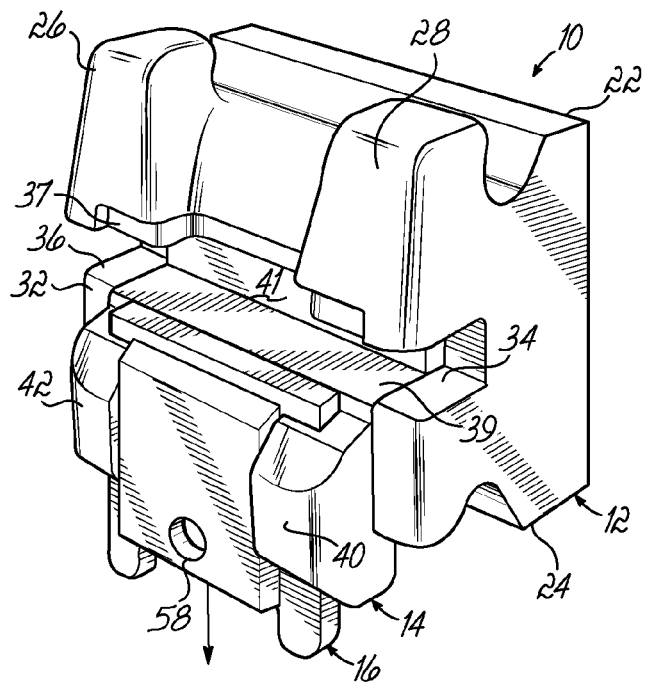
FIG. 3 is a perspective view similar to FIG. 2 in which the movable slide is in an unlatched condition affording access to the archwire slot.
Figure 4:
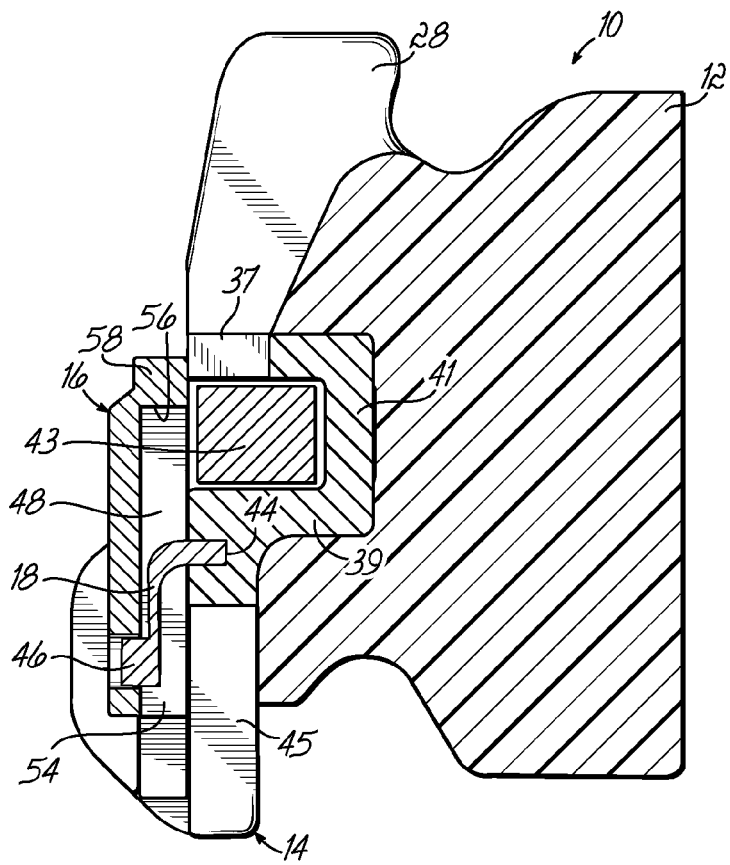
FIG. 4 is a cross-sectional view of the self-ligating orthodontic bracket of FIG. 2 shown with an archwire captured in the archwire slot.
Figure 5:
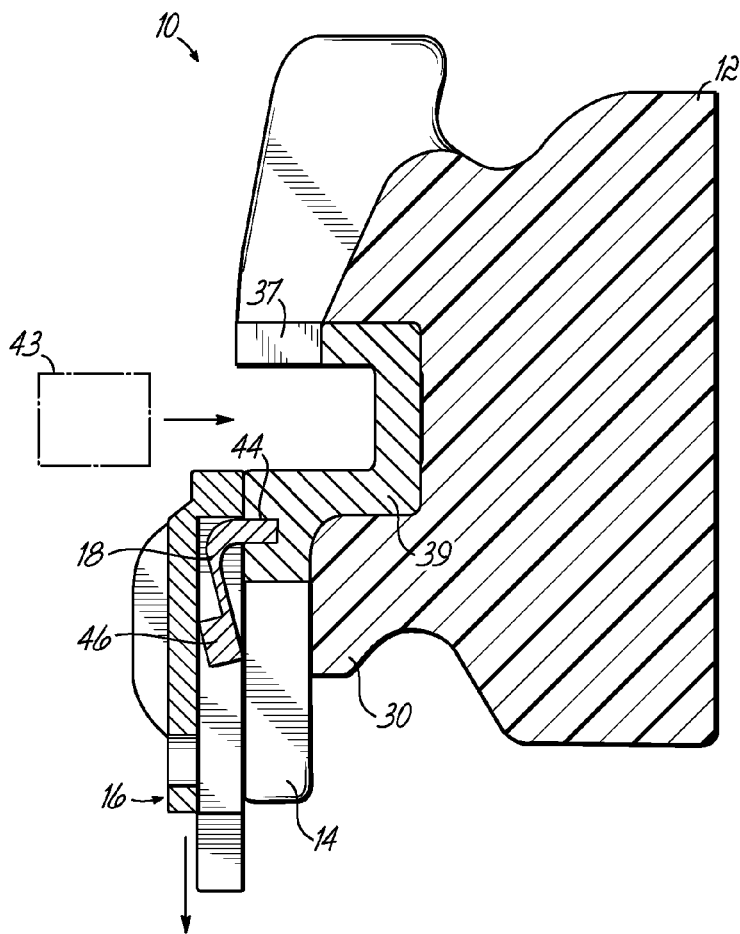
FIG. 5 is a cross-sectional view of the self-ligating bracket of FIG. 3.

With reference to FIGS. 1-5, an orthodontic bracket, generally indicated by reference numeral 10, includes a bracket body 12, a self-ligation insert 14 partially embedded or insert molded within the bracket body 12, a movable ligating slide 16 slidably coupled with the self-ligation insert 14, and a resilient engagement member or spring arm 18 that regulates the ability of the ligating slide 16 to move relative to the self-ligation insert 14. The spring arm 18 also locks the slide 16 in an open or unlatched position (FIG. 3) and a closed or latched position (FIG. 2). The bracket body 12 and self-ligation insert 14 collectively form an orthodontic bracket structure for use in corrective orthodontic treatments.

The bracket body 12 has a bonding base 20, an occlusal side 22 when mounted to a tooth carried by the patient's lower jaw, a gingival side 24, a plurality of, for example, two orthodontic tie wings 26, 28 formed on the gingival side of body 12, a pair of side flanges 30, 32, two spaced archwire slot portions 34, 36 defined occlusal/gingivally between each of the tie wings 26, 28 and a corresponding one of the side flanges 30, 32, and a recessed groove 33 extending in a mesial/distal direction between the side flanges 30, 32. The recessed groove 33 is aligned with the archwire slot portions 34, 36, which likewise extend in a mesial/distal direction. The tie wings 26, 28 are spaced in a mesial/distal direction and provide orthodontic attachment points to, for example, apply torsional forces to the tooth. The bonding base 20 of the bracket body 12 is configured to be secured to a tooth in any conventional manner, for example, by an appropriate orthodontic cement or adhesive.

With continued reference to FIGS. 1-5, the self-ligation insert 14 includes a base wall 41 and a pair of opposed slot walls 37, 39 projecting labially from the base wall 41 that collectively define an archwire slot 38 extending in a mesial/distal direction. The self-ligation insert 14 further includes a pair of guides 40, 42 positioned on respective mesial and distal sides above the archwire slot 38 and a planar member 45 extending from slot wall 39 and carrying the guides 40, 42. The guides 40, 42 are generally L-shaped and project outwardly from the planar member 45 in a labial direction. The slot walls 37, 39 and base wall 41 are substantially encapsulated or embedded within the material of the bracket body 12. The guides 40, 42 are positioned on the side of the archwire slot 38 opposite to the slot wall 37. The archwire slot 38 and the archwire slot portions 30, 32 of the bracket body 12 are collectively designed to receive an orthodontic archwire 43 (FIG. 4) in the same manner as typical prior art orthodontic brackets.

Opposite mesial/distal peripheral edges of the ligating slide 16 are movably and slidably engaged between the planar member 45 and the corresponding one of the mesial and distal guides 40, 42. The ligating slide 16 is movable occlusal/gingivally relative to the bracket body 12 between an open or unlatched position in which the arch wire 43 is insertable into the archwire slot 38 and a closed or latched position in which the arch wire 43 is captured or enclosed in the archwire slot 38. Slot wall 37 is recessed below the surrounding surface of the bracket body 12 so that, when the ligating slide 16 is in the closed position, a peripheral portion of the slide 16 contacts bracket body 12 on the side of the self-ligating insert 14 opposite to the attachment of the guides 40, 42.

The spring arm 18 regulates the movement of the ligating slide 16 relative to the bracket body 12 and self-ligating insert 14 and also prevents accidental or unintentional detachment of the ligating slide 12 from the self-ligation insert 14 during use regardless of whether the ligating slide 12 is left in an open or closed position. The spring arm 18 operates to couple the ligating slide 16 with the bracket body 12 and locates the ligating slide 12 relative to the bracket body 12 in the open and closed positions.

The spring arm 18 is generally L-shaped and is aligned perpendicularly relative to the archwire slot 38. One labially-extending end of the spring arm 18 is secured with the self-ligating insert 14 so that the spring arm 18 extends between the guides 40, 42 for mechanical coupling with a blind opening 44 formed in the planar member 45. The spring arm 18 may be secured to the self-ligating insert 14 or may merely be confined or trapped between the ligating slide 16 and the self-ligating insert 14. An opposite end of the spring arm 18 is provided with a labially-extending detent or projection 46, which may be, for example, rectangular or cylindrical in cross-section.

With continued reference to FIGS. 1-5, the ligating slide 16 is a generally planar structure having an elongate slot or recess 48 (FIG. 4) opening toward the tooth surface and configured for receiving the spring arm 18, a flange 50 extending outwardly in a mesial/distal direction from a side edge, a flange 52 extending outwardly in a mesial/distal direction from an opposite side edge, and a flange 53 extending labially/lingually. The flanges 50, 52 and 53 are arranged about the outer margin of the ligating slide 16. Flange 50 is engaged with guide 40 of the self-ligating insert 14 for sliding movement and flange 52 is slidingly engaged with the distal guide 42. Flange 53 of the ligating slide 38 abuts two outwardly-projecting portions of slot wall 37 that are spaced in the mesial/distal direction The elongated recess 48 has an open end 54 opening occlusally or gingivally and a closed wall 56 opposite the open end 54. Extending ligually/labially through the ligating slide 16 near the open end 54 is an aperture or opening 58, which corresponds in cross-sectional profile with the cross-sectional profile of the projection 46. The spring arm 18 is capable of resiliently cantilevering relative to the ligating slide 16 for selectively engaging the projection 46 with the opening 58 so as to lock the ligating slide 16 in its closed position. To that end, the spring arm 18 is resiliently biased in a direction that forces the projection 46 outwardly in a gingival direction away from the tooth and toward the ligating slide 16.

The spring arm 18 operates to retain ligating slide 16 in either the open or closed position and controls the release of the ligating slide 16 while the bracket 10 is worn on a tooth. To that end, the spring arm 18 provides positive stops for the ligating slide 16 in the open and closed positions without overcoming a biasing force during the transitions between the open and closed positions. In other words, the spring arm 18 locks the ligating slide 16 in the open and closed positions independent of the biasing force of the spring arm 18. The spring arm 18 merely operates for establishing the open position by coercing the projection 46 to engage opening 58 and the closed position by abutting against an inwardly-facing surface of closed wall 56.

In certain embodiments of the invention, the bracket body 12 may be made of any aesthetically-pleasing substantially transparent, translucent or tooth-colored material, such as a ceramic or a polymer resin. Suitable polymer resins include, but are not limited to, polycarbonate, acrylic-based thermoplastic resins, acrylic thermoset resins, and other structural plastics. The polymer resin may be reinforced or filled with a filler, such as glass spheres, or reinforcing fibers, such as glass fibers, to provide a composite that improves the rigidity and strength of the bracket body 12. Suitable ceramics include polycrystalline aluminum oxide, sapphire, toughened zirconia and yttrium-stabilized zirconia.

In these embodiments, the self-ligation insert 14 is made by any suitable forming technique, such as metal injection molding (MIM), from a biocompatible metal, such as a stainless steel and, more specifically, a 17-4 stainless steel. The spring arm 18 is made from any suitable material, including stainless steels, titanium alloys and Ni/Ti type superelastic materials. One particularly suitable material for spring arm 18 is 17-7 PH stainless steel. The ligating slide 16 may be formed by any suitable process, such as MIM, from any biocompatible material, including metals such as stainless steel, or as a metal core member surrounded at least partially by a thin shell of a ceramic, such as an aluminum oxide, titanium nitride or titanium oxide, colored to have the appearance of a natural tooth enamel and which may be shaded to correspond to the shading of a specific patient's enamel. The bracket body 12, the self-ligation insert 14, and the ligating slide 16 are assembled by any conventional molding technique, such as injection molding.

In other specific embodiments of the invention, the orthodontic bracket 10 may be formed entirely from metal without departing from the spirit and scope of the invention. In still other specific embodiments of the invention, the metallic self-ligating insert 14 may assume different constructions, such as a metallic hinged closure, and is not limited to a sliding ligating mechanism.

With reference to FIGS. 1-5, the ligating slide 16 in the closed position blocks the entrance to the archwire slot 38 to capture the archwire 43 therein and the engagement between projection 26 and opening 58 provides a latched condition. The ligating slide 16 unlocked using an end of a tool (FIG. 15) designed to press the projection 46 inwardly (i.e., lingually) toward the tooth with a force sufficient to overcome the bias applied by spring arm 18 and disengage the projection 46 from the opening 58 in the ligating slide 16 to provide an unlatched condition. When the projection 46 is moved by the tool inwardly (i.e., lingually) by a distance adequate to substantially clear the plane of the backside of the ligating slide 16, the ligating slide 16 is freely movable using a force applied by the tool occlusal/gingivally toward the open position in a slidable manner guided by guides 40, 42. The motion of the ligating slide 16 is positively stopped in the open position by contact between the bend 62 of the spring arm 18 and the closed wall 56 of the elongated recess 48.

To place the ligating slide 16 in the closed position, slide 16 is moved occlusal/gingivally until the projection 46 springs outwardly under the bias applied by spring arm 18 and is received in the opening 58. The ligating slide 16 is then securely locked in the closed position. The engagement of the projection 46 into the opening 58 may create a tactile effect which is perceptible to a clinician and/or emits an audible sound, such as a click, that is likewise perceptible by a clinician. The ligating slide 16 may be moved occlusal/gingivally using the tool described above or simply pushed occlusal/gingivally using a different type of tool, or the clinician's fingertip, by contact with the edge of flange 53 because the ligating slide 16 is freely movable occlusal/gingivally without overcoming the spring force applied by the spring arm 18.

The resilient bias applied by the spring arm 18 does not act on the ligating slide 16 other than to engage the projection 46 with the opening 58 and to locate the bend 62 relative to the closed end of the elongate recess 48. It follows that the spring arm 18 is not operatively coupled with the ligating slide 16 for providing a force that moves the ligating slide 16 relative to the bracket body 12. Moreover, the ligating slide 16 does not have to overcome the resilient force of the spring arm 18 during movement.

Figure 7:
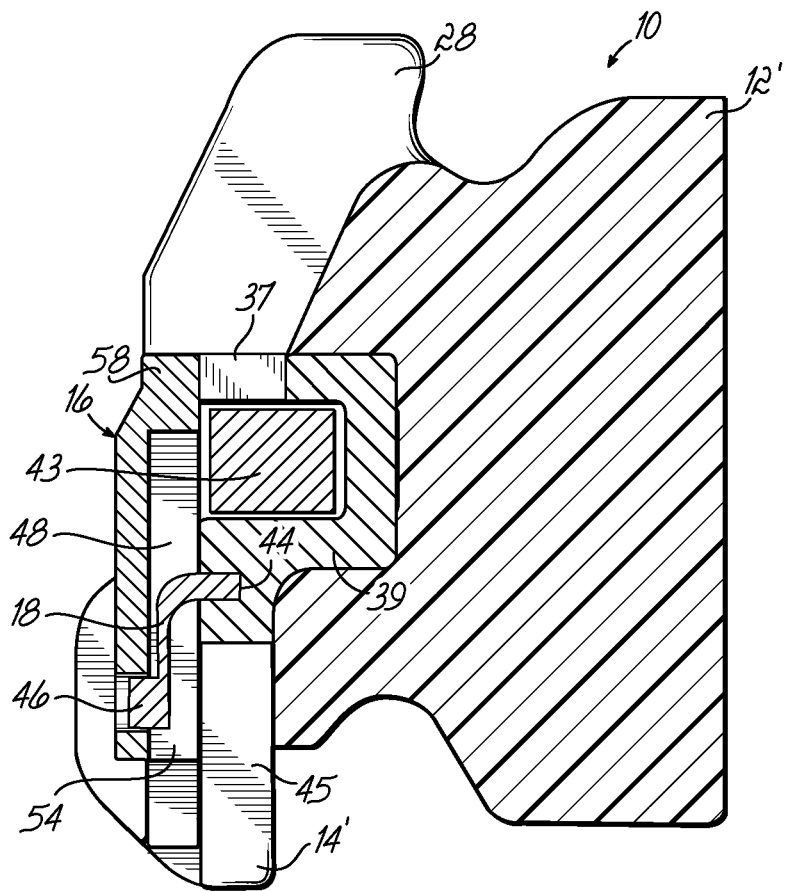
FIG. 7 is a view of another alternative embodiment of a self-ligating orthodontic bracket in accordance with the principles of the invention.

With reference to FIG. 7 and in an alternative embodiment, the tie wings 26, 28 may be redimensioned to project outwardly (i.e., labially) beyond or above the edge of slot wall 37. As a result, the leading exterior edge of the closed wall 56 abuts against the side of the tie wings 26, 28 when the ligating slide 16 is in the closed position.

Figure 6:
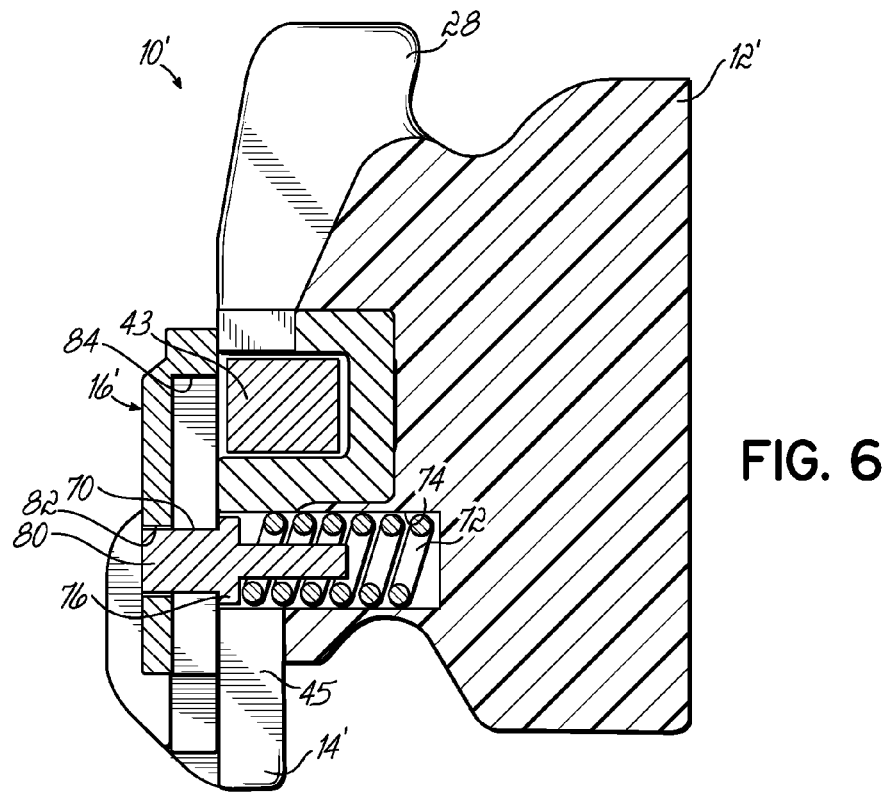
FIG. 6 is a view of an alternative embodiment of an orthodontic bracket according to the principles of the invention.

With reference to FIG. 6 in which like reference numerals refer to like features in FIGS. 1-5, an orthodontic bracket 10' in accordance with an alternative embodiment of the invention includes a bracket body 12', a self-ligation insert 14' embedded or insert molded within the bracket body 12', a movable ligating slide 16' slidably coupled with the self-ligation insert 14', and a resilient engagement member consisting of a pin 70 and a resilient member 72 that biases the pin 70 toward the ligating slide 16' for regulating the movement of the ligating slide 16' relative to the self-ligation insert 14'. The components of orthodontic bracket 10' are substantially similar to those of orthodontic bracket 10, other than noted below. The orthodontic bracket 10' is illustrated with the ligating slide 16' moved to a closed position in FIG. 6.

The bracket body 12' incorporates a cylindrical bore 74, which may be a blind bore, into which the resilient member 72, illustrated as a compression spring, is received. The resilient member 72 is captured in a compressed state between a collar 76 of the pin 70 and the closed end of blind bore 74. The compression of the resilient member 72 creates a labially-directed bias. Extending outwardly from the collar 76 is a cylindrical detent or projection 80. When the ligating slide 16' is in the closed position, a gingival side of the collar 76 contacts the underside of the slide 16' and the projection 80 is received in an aperture or opening 82 provided in the ligating slide 16'. The engagement between the projection 80 and opening 82 operates to retain ligating slide 16' in either the open or closed position and controls the release of the ligating slide 16' while the bracket 10' is worn on a tooth.

To provide an open position, the projection 80 is pressed inwardly toward the tooth using a tool (not shown) with a force sufficient to overcome the bias applied by resilient member 72 for disengaging the projection 80 from the opening 82. When the projection 80 is moved inwardly by a distance adequate to substantially clear the plane of the backside of the ligating slide 16', the ligating slide 16' may be moved slidably toward the open position. In the open position, the projection 80 contacts an end wall 84 of the recess to provide a positive stop such that the ligating slide 16' is captivated to the bracket body 12'. To move the ligating slide 16' from the open position to the closed position is accomplished by moving the slide 16' occlusal/gingivally until the projection 80 springs outwardly under the bias applied by resilient member 72 and is received in the opening 82. The ligating slide 16' is then securely locked in the closed position. The resilient member 72 is for the purpose of engaging and disengaging the member 72 into and out of the opening 82.

Figure 8:
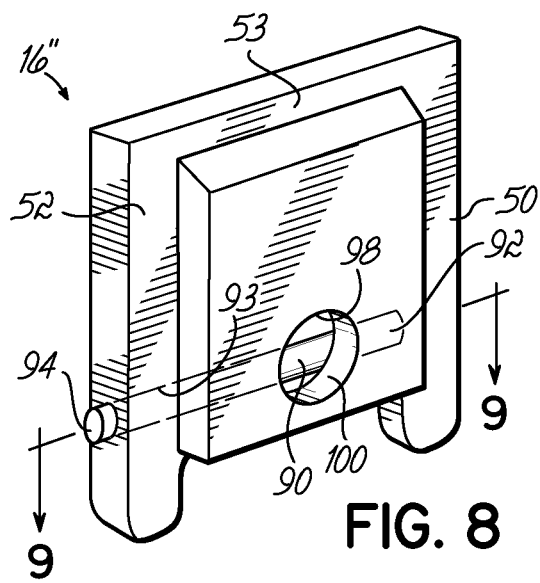
FIG. 8 is a view of another alternative embodiment of a self-ligating orthodontic bracket in accordance with the principles of the invention.
Figure 9:
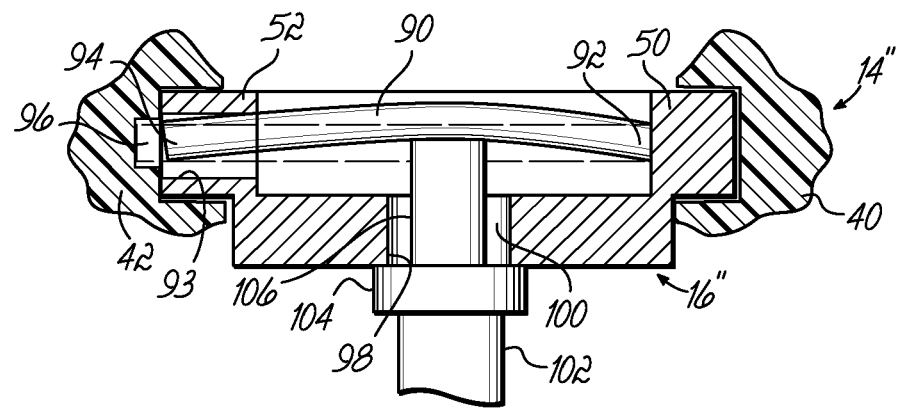
FIG. 9 is a cross-sectional view taken generally along line 9-9 in FIG. 8 in which the locking wire is deflected occlusal/gingivally.
Figure 10:
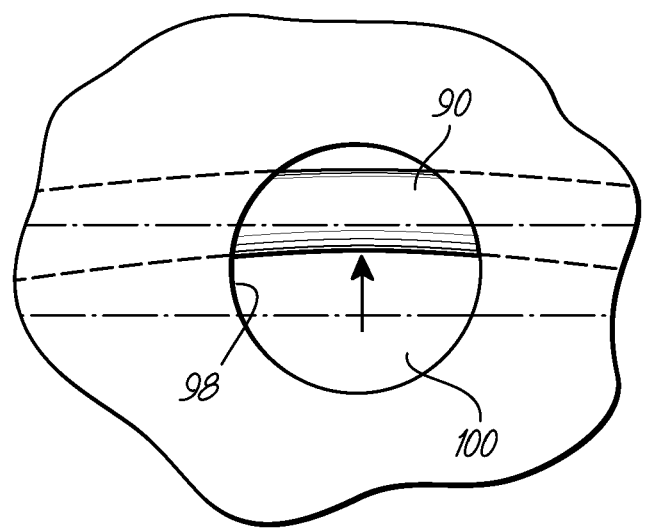
FIG. 10 is an enlarged view of a portion of FIG. 8 in which the locking wire is deflected inwardly toward the tooth.

With reference to FIGS. 8-10 in which like reference numerals refer to like features in FIGS. 1-5, an orthodontic bracket 10" in accordance with an alternative embodiment of the invention includes a self-ligation insert 14" embedded or insert molded within the bracket body (not shown), a movable ligating slide 16" slidably coupled with the self-ligation insert 14", and a resilient engagement member consisting of a locking wire 90 fixed at one end 92 to the ligating slide 16". The locking wire 90 extends in a mesial/distal direction through a passageway 93 formed in flange 52 of the ligating slide 16" and an opposite end 94 of locking wire 90 projects beyond the peripheral side edge of slide 16". In the closed position, end 94 of locking wire 90 extends into a complementary locking recess 96 formed in guide 42 so that end 94 operates as a detent to arrest or otherwise prevent movement of the ligating slide 16'. The engagement between end 94 and locking recess 96 provides a positive stop for the ligating slide 16" in the open position.

Extending through the thickness of the ligating slide 16" is an aperture or opening 98 within which a length of the locking wire 90 is located. To release the ligating slide 16" from the closed position, the locking wire 90 is bent or deflected using a suitable tool (not shown) occlusal/gingivally toward an inner edge 100 surrounding and defining the opening 98 so that end 94 of the locking wire 90 is withdrawn from the locking recess 96, as shown in FIG. 10. The ligating slide 16" is then freely movable using an occlusal/gingivally force applied by tool 102 from the closed position to the open position for inserting archwire 143 into the archwire slot 38. The locking wire 90 is formed from any material of sufficient bendability to permit repeated movements or deflections for withdrawing end 94 from the locking recess 96. More specifically, the material forming the locking wire 90 should undergo elastic deformation without significant plastic deformation when bent or deflected to withdraw end 94 from the locking recess 96. As a result, the locking wire 90 is capable of extending to engage the end 94 in locking recess 96 when the ligating slide 16" is moved from the open position to the closed position after the archwire 43 has been inserted in the archwire slot 38. The locking wire 90 may be constructed from, for example, a superelastic Ni/Ti alloy. It is contemplated that the locking wire 90 may be bent at about a 90° angle into an L-shape and attached to the ligating slide 16" with the bend visible in opening 98 such that a force applied to the locking wire 90 in a mesial/distal direction withdraws end 94 from locking recess 96.

FIG. 9 illustrates an alternative method of deflecting the locking wire 90 in order to remove end 94 from the locking recess 96 to release the ligating slide 16" so that slide 16" can be moved from its closed position to its open position. Specifically, the portion of the locking wire 90 visible in opening 98 is pushed inwardly (in a lingual direction) with one end 106 of a suitable tool having a collar 104 of a larger diameter than an inner diameter of opening 98 to limit the inward displacement of locking wire 90.

With reference to FIGS. 11-14 and in accordance with an alternative embodiment of the invention, an orthodontic bracket, generally indicated by reference numeral 110, for use in corrective orthodontic treatments includes a bracket body 112, a self-ligation insert 114 mounted in the bracket body 112, a movable ligating slide 116 slidably coupled with the self-ligation insert 114, and a resilient engagement member or spring arm 118. The bracket body 112, self-ligation insert 114, ligating slide 116 and spring arm 118 are formed from materials identical to the materials described above for corresponding components of orthodontic bracket 10 (FIGS. 1-5).

Figure 11:
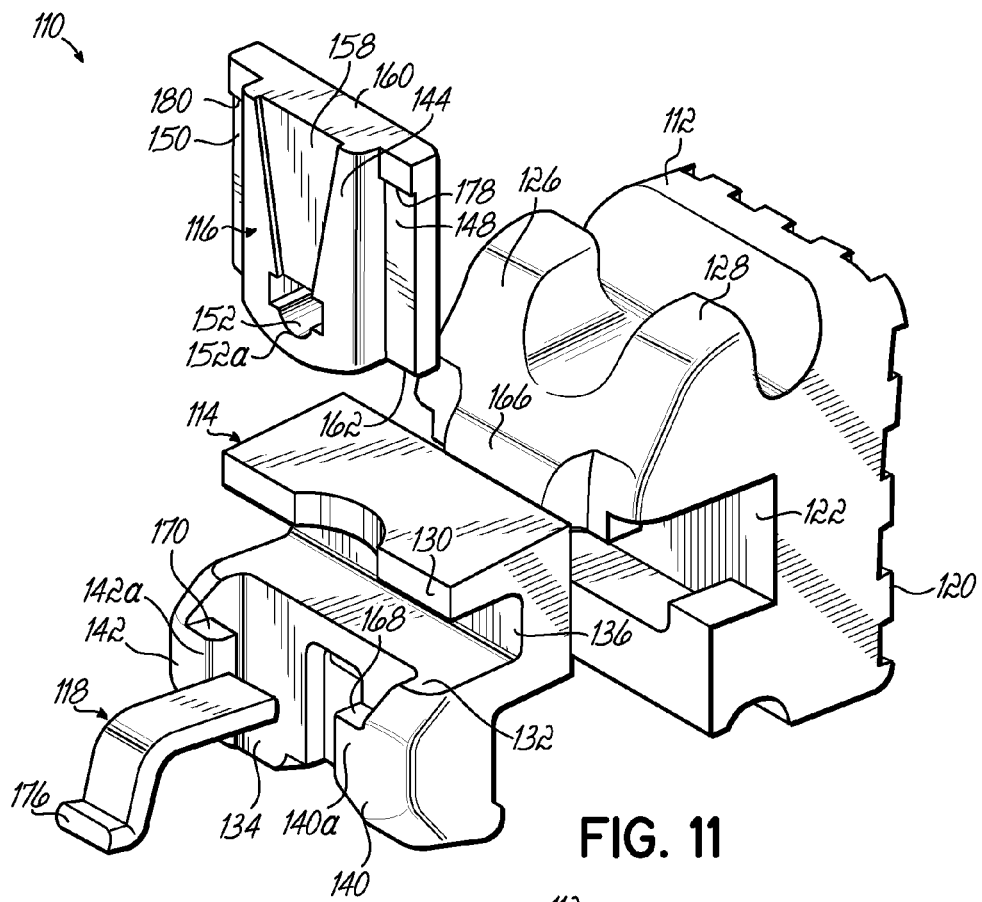
FIG. 11 is an exploded perspective view of another alternative embodiment of a self-ligating orthodontic bracket in accordance with the principles of the invention.
Figure 12:
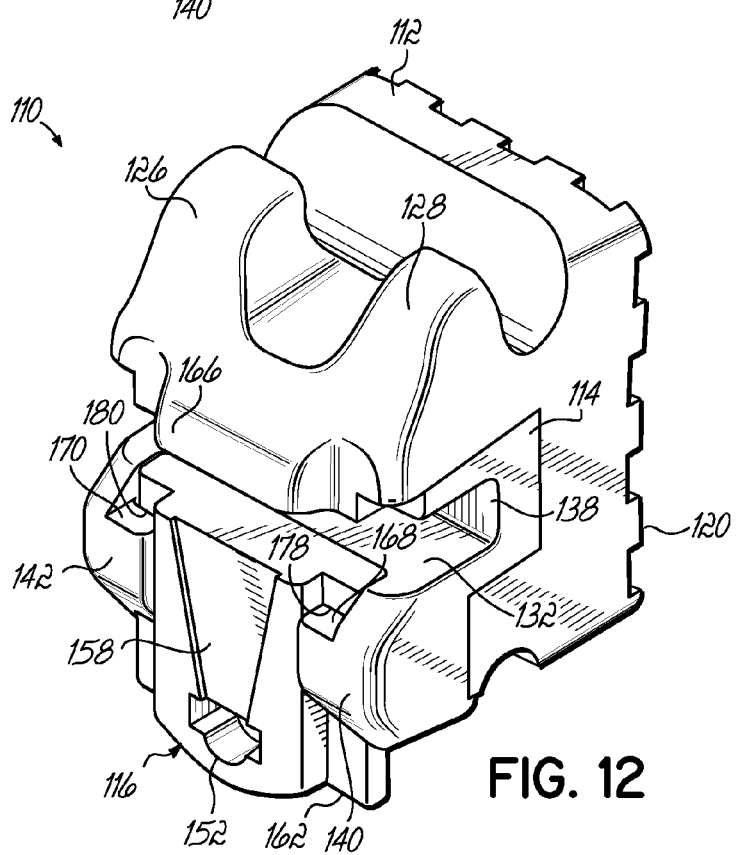
FIG. 12 is a perspective view of the self-ligating orthodontic bracket of FIG. 11 in which the movable slide is in an unlatched condition.
Figure 13:
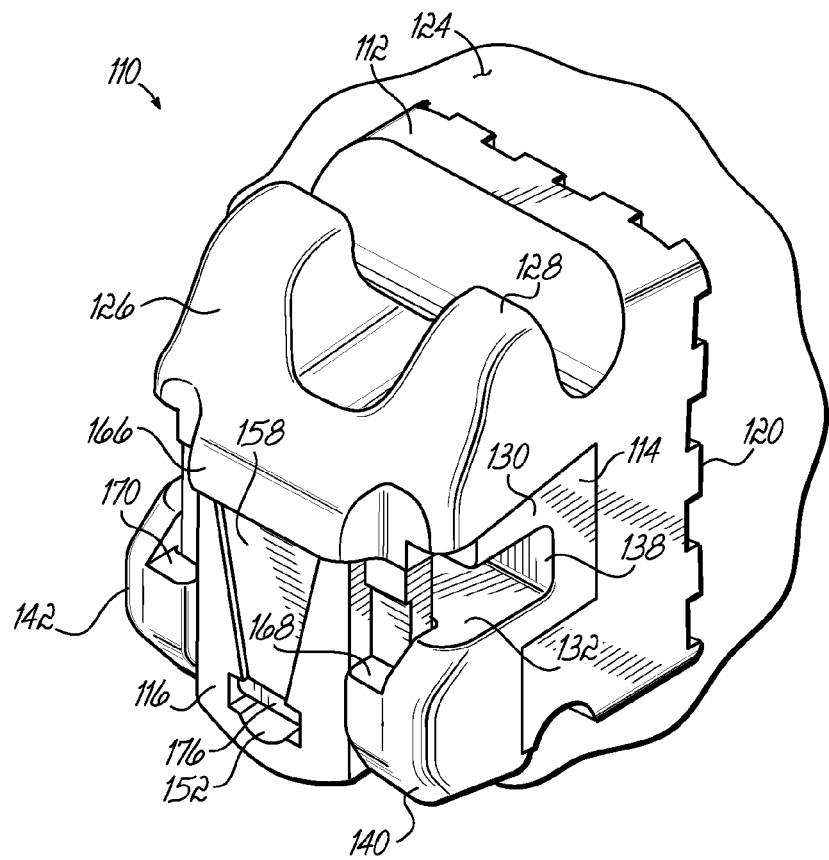
FIG. 13 is a perspective view of the self-ligating orthodontic bracket of FIG. 11 in which the movable slide is in a latched condition.

The bracket body 112 includes a bonding base 120 and a recessed slot or groove 122, best visible in FIG. 11, extending generally in a mesial/distal direction. The bonding base 120 is configured to be secured to the enamel of a tooth 124 in any conventional manner, for example, by an appropriate orthodontic cement or adhesive. More specifically, the bracket body 112 is typically secured to tooth 124 with an orientation such that gravity assists the movement of ligating slide 116 from a closed position (FIG. 13) defining a latched condition or to an open position (FIG. 12) defining an unlatched condition and helps to maintain the ligating slide 116 in the open position until a moving force is applied. When tooth 124 is carried by the patient's lower jaw, the bracket body 112 is bonded to the mandibular tooth 124 such that the ligating slide 116 moves in a gingival to occlusal direction when closing and, hence, slide 116 moves generally in the direction of gravity. When tooth 124 is carried by the patient's upper jaw, the bracket body 112 is bonded to the maxillary tooth 124 such that the ligating slide 116 moves in a occlusal to gingival direction when closing and slide 116 still moves generally in the direction of gravity.

Two orthodontic tie wings 126, 128 may be optionally provided on the bracket body 112 with a spaced relationship in a mesial/distal direction. Tie wings 126, 128 provide orthodontic attachment points to, for example, apply torsional forces to the tooth 124.

With continued reference to FIGS. 11-14, the self-ligation insert 114 includes a base wall 136 and a pair of opposed slot or side walls 130, 132 projecting outwardly in a labial or buccal direction from the base 136. The side walls 130, 132 and base wall 136 are embedded within the material of the bracket body 112 and generally coextensive with the groove 122 in the bracket body 112. The side walls 130, 132 and base wall 136 collectively define an archwire slot 138 extending generally in a mesial/distal direction. The archwire slot 138 is designed to receive an orthodontic archwire 143 (FIG. 14) in the same manner as conventional orthodontic brackets. Portions of the bracket body 112 overlie side wall 130 of self-ligation insert 114 to make the insert 114 resistant to a pullout force directed outwardly relative to tooth 124.

Figure 14:
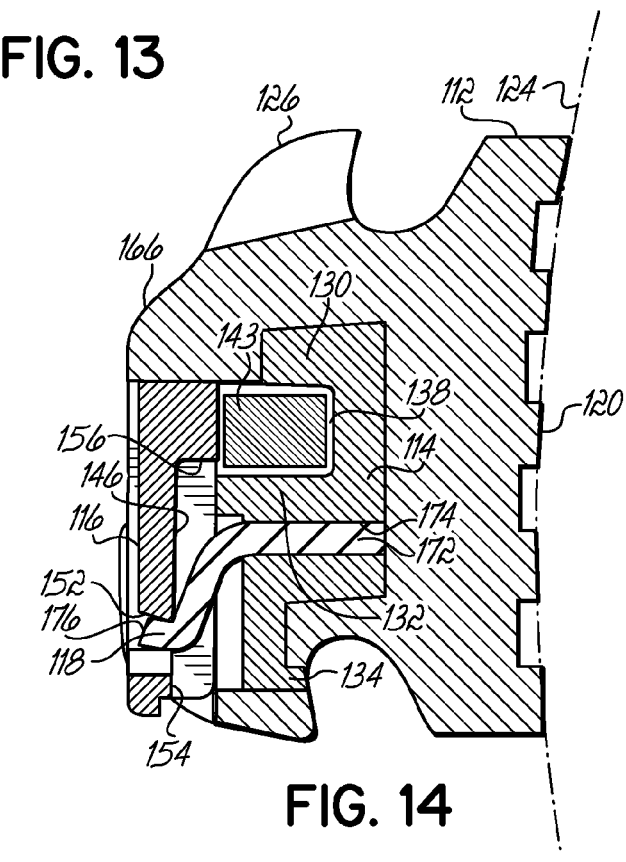
FIG. 14 is a cross-sectional view of the self-ligating orthodontic bracket of FIG. 13.

Side wall 130 has a wedge-shape, as most evident in FIG. 14, that operates to increase the pullout resistance of insert 114. The configuration of side wall 130 at the interface with the bracket body 112 creates a draft or reverse angle that tends to lock the insert 114 with bracket body 112. In particular, the draft increases the resistance of insert 114 to a pullout force directed outwardly from tooth 124.

The self-ligation insert 114 further includes a substantially planar member 134 extending from side wall 132 and a pair of guides 140, 142 carried by planar member 134. The guides 140, 142 are located with a spaced relationship in the mesial/distal direction. The guides 140, 142 project outwardly from the planar member 134 in a labial or buccal direction and are positioned on the side of the archwire slot 138. Guide 140 includes a lip 140a projecting in a mesial/distal direction that is oriented toward a lip 142a on guide 142 also projecting in a mesial/distal direction. Because the insert 114 includes guides 140, 142 formed from metal, the insert 114 has a strength sufficient to construct an orthodontic bracket 110 that is self-ligating.

With continued reference to FIGS. 11-14, the ligating slide 116 is a generally planar structure having a central portion 144, an elongated groove or recess 146 (FIG. 14) in the central portion that opens toward the tooth 124, a flange 148 extending outwardly in a mesial/distal direction from a side edge of central portion 144, and a flange 150 extending outwardly in a mesial/distal direction from an opposite side edge of central portion 144. Flanges 148 and 150 each are joined to the central portion 144 by a smoothly-curved junction. Flange 148 moves occlusal/gingivally in the C-shaped space between lip 140a of guide 140 of the self-ligating insert 114 and planar member 134. Similarly, flange 150 moves occlusal/gingivally in the C-shaped space between the lip 140b of guide 142 and planar member 134.

Elongated recess 146 extends between an open end 154 and a closed end 156 opposite the open end 154. A throughhole or aperture 152 is formed near the open end 154. A labial side of the central portion 144 of the ligating slide 116 includes a channel 158 that tapers or narrows in a direction from a leading edge 160 of slide 116 toward a trailing edge 162 of slide 116. Aperture 152 is located near, and usually at, the apex of the channel 158, which converges toward aperture 152. Channel 158 is on a surface of the central portion 144 opposite to the surface bearing elongate recess 146. Channel 158 may be oriented and configured in any manner sufficient to guide tip 184 (FIG. 15) toward aperture 152, as described below. For example, channel 158 may lack tapering or aperture 152 may have a location other than near the apex of channel 158.

With continued reference to FIGS. 11-14, the ligating slide 116 is movable occlusal/gingivally relative to the bracket body 112 between open and closed positions. In the open position, the archwire slot 138 is accessible for inserting an arch wire 143 (FIG. 14) into the archwire slot 138 and the closed position in which the arch wire 143 is captured or enclosed in the archwire slot 138. When the ligating slide 116 is in the closed position, the leading edge 160 of the slide 116 is located adjacent to, and underlies, a smoothly-curving deflecting element 166 disposed on bracket body 112 generally between the tie wings 126, 128. Deflecting element 166 operates during chewing to cover and shield the leading edge 160 of the slide 116 from the chewed material in the patient's oral cavity. As a result, the chewed material cannot contact the leading edge 160, which increases the resistance of slide 116 to movement during chewing. The invention contemplates deflecting element 166 may be a continuous ridge, as depicted in FIGS. 11-14, or may have other constructions adequate to shield leading edge 160, such as an aligned row of discontinuous and spaced-apart projections. In any event, the smooth convex curvature of the deflecting element 166 deflects chewed material or other objects in a direction away from leading edge 160.

When the ligating slide 116 is in the open position, portions of the trailing edge 162 of the slide 116 abut against stops 168, 170 formed on guides 140, 142, respectively, each having the form of a substantially flat surface. Stops 168, 170 prevent accidental or unintentional detachment of the ligating slide 112 from the self-ligation insert 114 during use when the ligating slide 112 is positioned in the open position. The stops 168 and 170 collectively limit the occlusal/gingival range of movement of the ligating slide 116.

With continued reference to FIGS. 11-14, the spring arm 118 regulates the movement of the ligating slide 116 relative to the bracket body 112 and self-ligating insert 114 is confined or trapped between the self-ligating insert 114 and the ligating slide 116. The spring arm 118 is generally L-shaped and is aligned generally perpendicularly relative to the archwire slot 138. An inwardly-extending prong 172 of the spring arm 118 is received in a recess 174 formed in the self-ligating insert 114. The free end of the spring arm 118 is provided with an outwardly-extending detent or projection 176, which corresponds generally in cross-sectional profile with the cross-sectional profile of the aperture 152 and, to that end, may be rectangular or oval-shaped in cross-section. The projection 176 extends into aperture 152 in the ligating slide 116 when slide 116 is located in the closed position. The engagement between the projection 176 and the aperture 152 holds the ligating slide 116 in the closed position against movement that would otherwise open the slide, assisted by deflecting element 166 which shields the leading edge 160 of ligating slide 116 from contact with chewed material. As a result, ligating slide 116 is unlikely to be unintentionally moved from the closed position to the open position.

The free end of spring arm 118 carrying projection 176 is elastically compressed when captured within the elongated recess 146. Specifically, the free end of spring arm 118 is capable of resiliently flexing or deforming outwardly toward the ligating slide 116, when the projection 176 is aligned with aperture 152, for selectively engaging the projection 176 with the aperture 152 so as to lock the ligating slide 116 in its closed position. To that end, the spring arm 118 is resiliently biased in a direction that forces the projection 176 outwardly away from the tooth and toward the ligating slide 116.

The ligating slide 116 includes a pair of projections or stops 178, 180 in the form of substantially flat surfaces that are oriented to face the stops 168, 170, respectively, on the insert 114. When the ligating slide is fully open, stops 178, 180 each contact and abut against a corresponding one of the stops 168, 170 to provide a positive movement obstruction. The projection 176 of spring arm 118 contacts the elongated recess 146 in the open position with a force sufficient to maintain the ligating slide 116 in the open position in opposition to a lesser force applied occlusal/gingivally.

The ligating slide 116 is moveable between the open and closed positions without overcoming a significant biasing force during the transition between open and closed positions. In other words, the spring arm 118 locks the ligating slide 116 in the open and closed positions substantially independent of the biasing force of the spring arm 118. In positions between open and closed, the ligating slide 116 is freely movable by a force significantly less than the force required to move spring-biased slides of conventional self-ligating brackets. The ligating slide 116 is captivated with the insert 114 regardless of whether slide 116 is in the open or closed position.

Figure 15:
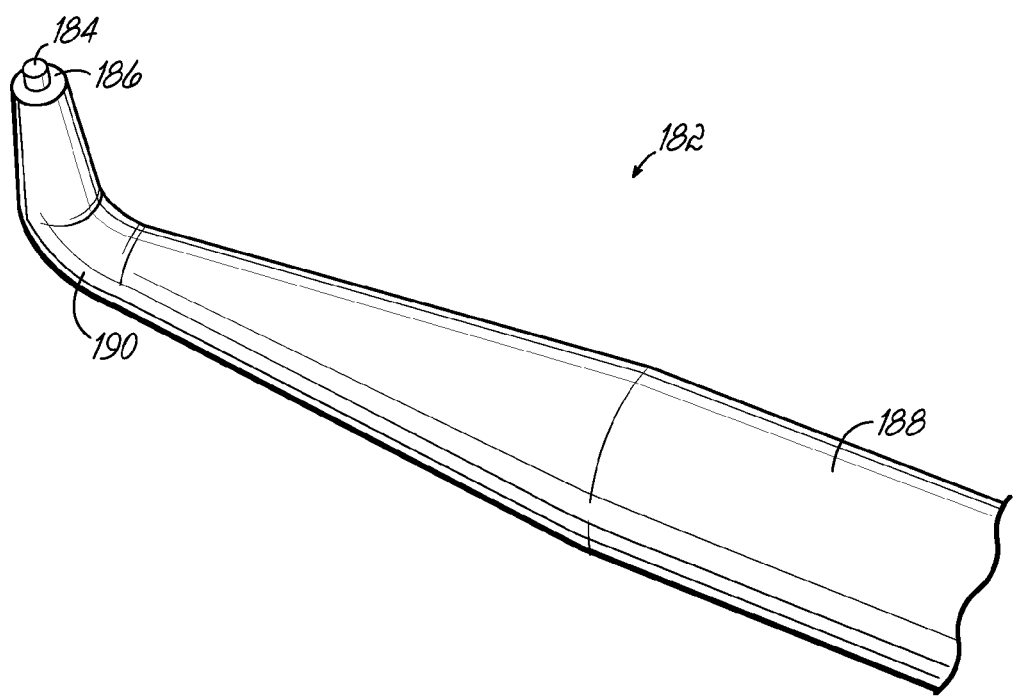
FIG. 15 is a perspective view of a portion of a tool suitable for moving the movable slide between latched and unlatched conditions.

With reference to FIG. 15, a spring release tool 182 includes a tip 184, an annular collar or shoulder 186 surrounding the tip 184, and a handle 188 for gripping and manipulating the tool 182. The tip 184 is inserted into the aperture 152 in the ligating slide 116 and, when pressed inward, forces the projection 176 inwardly to disengage the projection 176 from the aperture 152 and allow the ligating slide 116 to be moved from the closed position to the open position. As visibility inside the mouth is limited and the aperture 152 is a relatively small feature, the channel 158 operates to guide the tip 184 toward the aperture 152. Aperture 152 includes a curved portion 152a that aids in centering the tip 184 in aperture 152.

The handle 188 tapers toward a curved bend 190 that orients the tip 184 for accessing brackets 110 mounted to distal teeth 124. Bend 190 may be reduced in angle or omitted from spring release tool 182 for accessing mesial teeth 124 that are more accessible.

The shoulder 186 operates to limit the depth of insertion of tip 184 into the aperture 152 by contacting portions of the ligating slide 116 surrounding aperture 152. Specifically, the projection of tip 184 beyond shoulder 186 is limited such that a damaging force cannot be applied to the spring arm 118. Generally, the insertion depth is greater than or equal to the thickness of the slide surrounding aperture 152 but less than a distance that would apply a damaging force. In one embodiment, the tip 184 projects from shoulder 186 by a distance substantially equal to the thickness of the slide 166 surrounding the aperture 152. In one specific embodiment, tip 184 projects 0.01" from the shoulder 186 so that the maximum penetration distance of tip 184 into the aperture 152 is 0.01". If spring arm 118 is deflected by a distance substantially greater than required to disengage projection 176 from aperture 152, the spring arm 118 may be stressed beyond the elastic limit of the material and thereby damaged.

The invention contemplates that a channel similar to channel 158 may be used for other purposes on an orthodontic bracket, similar to orthodontic bracket 110, or other dental appliance to guide the tip of a tool to a defined destination on a ligating slide 116 or other structure. Therefore, this aspect of the invention is not limited to directing a tool tip 184 to aperture 152 and depressing a projection 176 from an aperture 152. In certain embodiments of the invention, the aperture 152 may be used to apply an inward force with tool tip 184 to disengage the projection 176 from a recess (not shown) formed in the ligating slide 116 that is separate and distinct from aperture 152.

In use and with reference to FIGS. 11-15, the ligating slide 116 in the closed position blocks access to the archwire slot 138 to captivate the archwire 143 therein. The ligating slide 116 is unlocked by placing the tip 184 of the spring release tool 182 generally in the channel 158 and moving tip 184 toward the aperture 152. The tapering of the channel 158 guides the tip 184 into the aperture 152. When the tip 184 is positioned within aperture 152, an inward force is applied by the tip 184 to projection 176 sufficient to overcome the bias applied by spring arm 118 and to disengage the projection 176 from the aperture 152. The ligating slide 116 is movable using a force applied by the tip 182 occlusal/gingivally toward the open position in a slidable manner guided by cooperation between the flanges 148, 150 and guides 140, 142. The motion of the ligating slide 116 is positively stopped in the open position by contact between the stops 178, 180 on ligating slide 116 and stops 168, 170 on the insert 114.

The ligating slide 116 is freely movable occlusal/gingivally from the open position to the closed position without overcoming the spring force applied by the spring arm 118. To place the ligating slide 116 in the closed position, slide 116 is moved occlusal/gingivally using tool 182 or the clinician's finger until the projection 176 springs outwardly under the bias applied by spring arm 118 into aperture 152. The ligating slide 116 is then securely locked in the closed position. The engagement of the projection 176 into the aperture 152 may create a tactile effect, which is perceptible to a clinician, and/or emits an audible sound, such as a click, that is likewise perceptible by a clinician. The resilient bias applied by the spring arm 118 does not act on the ligating slide 116 other than to engage the projection 176 with the aperture 152. It follows that the spring arm 118 is not operatively coupled with the ligating slide 116 for providing a force that moves the ligating slide 116 relative to the bracket body 112. Moreover, the ligating slide 116 does not have to overcome the resilient force of the spring arm 118 during movement.

While the invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicants' general inventive concept.

Having described the invention, what is claimed is:

1. An orthodontic bracket for coupling an archwire with a tooth, the orthodontic bracket comprising:
    a bracket structure configured to be mounted to the tooth, the bracket structure including an archwire slot configured to receive the archwire therein and a receiving portion;
    a movable member engaged with the bracket body and including a mesial flange, a distal flange, and a recess separating the mesial flange from the distal flange and a passage extending through at least one of the mesial flange and the distal flange, the movable member configured to be moved between an opened position in which the archwire is insertable into the archwire slot and a closed position in which the movable member retains the archwire in the archwire slot; and
    a wire carried by the movable member in the passage and being configured to engage the receiving portion when the movable member is in at least the closed position and to deform during movement of the movable member.

2. The orthodontic bracket of claim 1 wherein the wire and the archwire slot are oriented in a common direction relative to the bracket structure.

3. The orthodontic bracket of claim 1 wherein the passage is aligned parallel with the archwire slot.

4. The orthodontic bracket of claim 1 wherein the wire includes an end that projects out of the movable member, and the receiving portion is configured to receive the end of the wire.

5. The orthodontic bracket of claim 1 wherein the wire is physically coupled with the movable member.

6. The orthodontic bracket of claim 5 wherein the wire includes an end that projects out of the movable member.

7. The orthodontic bracket of claim 6 wherein the bracket structure includes a bracket body and an insert coupled with the bracket body, the insert including the archwire slot, and the receiving portion is located in the insert.

8. The orthodontic bracket of claim 7 wherein the receiving portion is a recess.

9. The orthodontic bracket of claim 1 wherein the movable member is a ligating slide.

10. The orthodontic bracket of claim 1 wherein the wire is comprised of a material that can be elastically deformed to permit movement of the movable member from the closed position to the opened position.

11. The orthodontic bracket of claim 10 wherein the wire is configured to elastically deform in response to an applied force so that the movable member is released to permit selective movement of the movable member relative to the bracket structure.

12. The orthodontic bracket of claim 1 wherein deformation of the wire includes a change in an overall length dimension of the wire between the opened position and the closed position.

13. The orthodontic bracket of claim 1 wherein a portion of the wire extends into the recess and is elastically bent during movement of the movable member between the opened position and the closed position.

14. The orthodontic bracket of claim 1 wherein an end portion of the wire extends from the movable member and deforming the wire retracts the end portion from the receiving portion of the bracket structure.

* * * * *